United States Patent [19]

Lim et al.

[11] Patent Number: 5,270,452
[45] Date of Patent: Dec. 14, 1993

[54] PURE GLIA MATURATION FACTOR

[75] Inventors: Ramon Lim, Iowa City, Iowa; Ruth Kaplan, West Chester; Michael Jaye, Glenside, both of Pa.

[73] Assignee: Rhone-Poulenc Rorer Pharmaceuticals Inc., Collegeville, Pa.

[21] Appl. No.: 785,185

[22] Filed: Oct. 31, 1991

Related U.S. Application Data

[63] Continuation of Ser. No. 692,772, Apr. 26, 1991, abandoned, which is a continuation of Ser. No. 276,847, Nov. 28, 1988, abandoned.

[51] Int. Cl.[5] ............... C07K 13/00; C12P 21/02; C12N 15/00
[52] U.S. Cl. ............... 530/399; 530/350; 435/172.3; 435/252.3; 435/320.1; 435/69.1
[58] Field of Search ............... 435/172.3, 69.1; 530/399

[56] References Cited

PUBLICATIONS

"Purification and Characterization of Glia Maturation Factor: A Growth Regulator for Neurons and Glia", Lim, R., et al., *Proc. Nat'l. Acad. Sci. USA* 86: 3901–05 (1989).

Watson, J. D. et al., Recombinant DNA A Short Course, Freeman and Co. N.Y., N.Y. 1983.

Gray, P. W. et al., 'Cloning and Expression of cDNA for human lymphotoxin, a lymphokine with Tumor Necrosis Activity', *Nature*, vol. 312, 20/27, Dec. 1984, pp. 721–724.

Lim R. et al. 'Purification of Bovine Glia Maturation Factor and Characterization with Monoclonal Antibody', *Biochemistry*, 24, pp. 8070–8074, 1985.

Pouwel, P. H. et al., Cloning Vectors, A Laboratory Manual, Elsevier 1985.

*Primary Examiner*—Marian C. Knode
*Attorney, Agent, or Firm*—Rosanne Goodman; Martin F. Savitzky

[57] ABSTRACT

Pure homogeneous glia maturation factor is disclosed with methods for producing it from neutral sources and by molecular cloning and genetic engineering.

13 Claims, 6 Drawing Sheets

```
                        10
T12= ETNNAAIIMK
T13= NKLVQTAELT K
T14= VFEIR
T15= FIVYSYK
T17= LGFFH
T18= NTEDLTEEWL R       20
T24= LVVLDEELEG ISPDELKDEL PER
T28= VSYPLCFIFS SPVGCKPEQQ MMYAGSK
```

FIG.5

FIG.6a  T18    N T E D L T E E W L
        5' AACACAGAGGACCTGACAGAGGAGTGGCT 3'

FIG.6b  T24    D E E L E G I S P D E L K D E L P E
        5' GATGAGGAGCTGGAGGGCATCTCCCCTGATGAGCTGAAGGATGAGCTGCCTGAG 3'

FIG.6c  T28    P V G C K P E Q Q M M Y A G
        5' CCTGTGGGCTGCAAGCCTGAGCAGCAGATGATGTATGCTGG 3'

```
  1 G AAT TCG GGG GGC GAC AGG CCG CTG ACG GCC GGA AGG AAA ATG AGT
      N   S   G   G   D   R   P   L   T   A   G   R   K  [M]  S

47 GAG TCT TTG GTT GTT TGT GAT GTT GCC GAA GAT TTA GTG GAA AAG
     E   S   L   V   V   C   D   V   A   E   D   L   V   E   K

92 CTG AGA AAG TTT CGT TTT CGC AAA GAA ACG AAC AAC GCT GCT ATA
     L   R   K   F   R   F   R   K   E   T   N   N   A   A   I

137 ATA ATG AAG ATT GAC AAG GAT AAA CGC CTG GTG GTA CTG GAT GAG
     I   M   K   I   D   K   D   K   R   L   V   V   L   D   E

182 GAG CTT GAG GGC ATT TCA CCA GAT GAA CTT AAA GAT GAA CTA CCT
     E   L   E   G   I   S   P   D   E   L   K   D   E   L   P

227 GAA CGA CAA CCT CGC TTC ATT GTG TAT AGT TAT AAA TAT CAA CAT
     E   R   Q   P   R   F   I   V   Y   S   Y   K   Y   Q   H

272 GAT GAT GGA AGA GTT TCA TAT CCT CTG TGC TTT ATT TTC TCC AGT
     D   D   G   R   V   S   Y   P   L   C   F   I   F   S   S

317 CCT GTT GGA TGT AAG CCT GAA CAA CAG ATG ATG TAT GCT GGA AGT
     P   V   G   C   K   P   E   Q   Q   M   M   Y   A   G   S

362 AAG AAT AAG CTA GTC CAG ACA GCT GAA CTA ACC AAG GTA TTT GAA
     K   N   K   L   V   Q   T   A   E   L   T   K   V   F   E

407 ATA AGA AAT ACC GAA GAC CTA ACT GAA GAA TGG TTA CGT GAG AAA
     I   R   N   T   E   D   L   T   E   E   W   L   R   E   K

452 CTT GGA TTT TTT CAC TAA TGTGAACTTC TGTGTTTCTA AAGTATTTAT
     L   G   F   F   H   •

500 GTATTAACCT GACCATACTG GAATCAGACA TAAATACTTA TTTATGCCTA

550 AAAATGCACT GTTACTTACA GTTTGTTTCC TGCAGTAAAG AAAAATTCTT

600 CATTTGTGCA AAATTTGAAC AAAGAGGAAA TCATCTTCAT AGTAATGAAA

650 CTTTGTAAAG TGTTTCCTTA TATTGGTAAT TGTTAGGTGG ACTACTTTTC CC
```

FIG.7

PURE GLIA MATURATION FACTOR

This is a continuation of application Ser. No. 07/692,772 filed on Apr. 26, 1991, which is a continuation of application Ser. No. 07/276,847 filed on Nov. 28, 1988, both now abandoned.

FIELD OF THE INVENTION

The present invention is directed to pure homogeneous glia maturation factor and processes for its production.

BACKGROUND OF THE INVENTION

Glia maturation factor (hereinafter GMF) is a protein, found in the brain of many animals, including man, which is capable of regulating the growth, development and differentiation of cells of neural origin (neurons and glia) and possibly other cell types. The term "glia maturation factor" (GMF), as used herein, includes both the crude preparations of GMF and pure GMF, whereas the term "glia maturation factor" (hereinafter GMF), as used herein, specifically denotes pure homogeneous GMF protein identifiable by a defined amino acid sequence.

GMF was discovered by Ramon Lim in 1972. Over the years, several biological functions have been identified for GMF, suggesting GMF as a potential therapeutic agent for a number of diseases or pathologic conditions in humans and animals. These functions are summarized as follows:

(1) Evidence that GMF can enhance nervous system regeneration. Lim & Miller (*Experientia*, 41: 412–415 (1985)) have shown that in newborn rats sustaining brain injury, GMF treatment prevents atrophy of the brain. In another instances, Lim, Miller & Toffano (*Trans. Am. Soc. Neurochem.*, 16: 307 (1985)) reported that when rat brains are transacted in the nigro-striatal region, injection of GMF into the brain helps the recovery as monitored by the neuron-specific enzyme tyrosine hydroxylase. Palatucci et al. (*Soc. Neurosci. Abstr.*, 14: 584 (1988)) demonstrated that in rats sustaining caudate lesion in the brain, treatment with GMF enhances recovery from behavioural deficit. Nieto-Sampedro et al. (*Neurosci. Letters*, 86: 361–365 (1988)) demonstrated that there is an enhanced release of GMF from the injury site in the brain. Lim et al. (*Trans. Am. Soc. Neurochem.*, 19: 83 (1988)) demonstrated that there is increased production of GMF in the satellite cells surrounding the sciatic nerve after the nerve is cut. The above suggests that GMF is involved in the regeneration of the nervous system. Thus, GMF is a potentially useful therapeutic agent for injuries to the brain, spinal cord and the nerves.

(2) Evidence that GMF can enhance nervous system development. The fact that GMF promotes regeneration of the nervous system suggests the possibility that it can promote the development of the nervous system, since development and regeneration involve similar mechanisms. Other evidence supports a role for GMF in development. For example, using a monoclonal antibody designated G2-09 specifically directed toward GMF, Lim et al. (*Dev. Brain Res.*, 33: 93–100 (1987)) found that the level of GMF is highest in embryonic brain. In tissue culture, GMF can stimulate the differentiation of astrocytes (Lim et al., *Science*, 195: 195–196 (1977)) and Schwann cells (Bosch et al., *Brain Res.*, 304: 311–319 (1984)). Lim et al. (*Trans. Am. Soc. Neurochem.*, 16: 307 (1985)) observed that when neurons are isolated from the mesencephalon region of the brain and grown in culture, GMF can stimulate them to take up neurotransmitters, a function characteristic of mature neurons.

GMF helps in the survival of neurons isolated from the cerebellum region of the brain (Guo & Lim, unpublished data). Lim, Miller & Zaheer (*Proc. Nat'l. Acad. Sci. USA* 86:3901–05 (1989)) found that GMF promotes the differentiation of neuronal tumors by causing them to grow out cell processes (neurites) while at the same time suppressing their proliferation (FIG. 1). Currently, there is not satisfactory treatment for children with abnormal development of the nervous system. Such pathologic conditions often lead to impairment of mental, behavioral or motor activities. GMF can potentially correct such developmental problems.

(3) Evidence that GMF can arrest or reverse the progress of nervous system degeneration. It is known that many neurological diseases are due to premature or abnormal degeneration of certain areas of the nervous system. Such pathologic conditions include Parkinson's disease and Alzheimer's disease and are difficult to treat. Although GMF has not been tested for these neurologic problems, it is conceivable that GMF may help in arresting or reversing the progression of such degenerative processes, given its regulatory role in brain cell development.

(4) Evidence that GMF can arrest or reverse the progress of tumors. It has been documented that GMF can suppress the growth of tumor cells derived from Schwann cells (Lim et al., *Proc. Natl. Acad. Sci.*, 78: 4373–4377 (1981)) and from astrocytes (Lim et al., *Cancer Res.*, 46: 5241 $\propto$ 5247 (1986)). Lim, Miller and Zaheer (*Proc. Nat'l. Acad. Sci. USA* 86:3901–05 (1989)) found that GMF also causes growth arrest in tumor cells of neuronal origin (FIG. 1). While it is clear that GMF exhibits an anticancer effect on brain tumors, it remains possible that the effect may extend to other types of tumors found elsewhere in the body, provided that the tumors develop receptors for GMF and are thus responsive to it. GMF could be an excellent therapeutic agent for all these tumors, not only as a direct growth suppressive agent, but also as a carrier for tumor destructive agents to reach the cancer site.

In order for GMF to be therapeutically useful, it must be purified to homogeneity, free of other proteins or compounds that may interfere with the action of the agent or cause untoward reactions on the recipient person or animal. GMF obtained by former purification procedure devised by Lim et al. (*Biochemistry*, 24: 8070–8074 (1985)), although appearing as one band on sodium dodecyl sulfate polyacrylamide gel electrophoresis (SDS-PAGE), did not turn out to be homogeneous and no amino acid sequence was able to be obtained. In the current invention, important changes were made on the procedure. Such changes led to the production of a pure homogeneous GMF protein, called GMF, which exhibits a definitive amino acid sequence. The sequence enabled us to clone the cDNA from a human source. From the cDNA we are able to produce recombinant GMF free of other proteins of human origin in large quantities using genetic engineering technology. For human application, GMF of the human type is preferred to that of other species because of possible immune reaction due to species difference.

Alternative ways to purify GMF may be possible, such as the use of affinity chromatography utilizing antibodies against GMF, or using specific lectins if GMF binds to such substances. However, none of these will be comparable in efficiency to the recombinant DNA method. Nevertheless, it is conceivable that GMF produced by the recombinant method may need to incorporate one or several of these other methods in its final purification.

SUMMARY OF THE INVENTION

In accordance with the present invention, a homogeneous GMF protein, designated GMF, has now been prepared. The purified homogeneous GMF protein is biologically active and has an apparent molecular weight of about 17,000 as determined by the SDS-PAGE procedure. The N-terminus is blocked, but tryptic digestion yielded several peptides from which a partial amino acid sequence has been constructed. This sequence serves as the definitive identification of the GMF protein. From the partial sequence, oligonucleotide probes have been synthesized to screen a human brain stem cDNA library, resulting in the cloning of the cDNA for GMF. The cloned cDNA was sequenced and the complete amino acid sequence of the GMF protein has been deduced. The deduced sequence contains 142 amino acid residues and matches the partial sequence of the natural GMF. The cloning of GMF enables the production of recombinant protein on a commercial scale.

Recombinant GMF is produced by a process which comprises (a) preparing a replicable expression vector capable of expressing the DNA sequence encoding GMF in a suitable host cell system; (b) transforming said host system to obtain a recombinant host system; (c) maintaining said recombinant host system under conditions permitting expression of said GMF encoding DNA sequence to produce GMF protein; and (d) recovering said GMF protein. Preferably, the GMF encoding replicable expression vector is made by preparing a ds-cDNA preparation representative.

The GMF is identifiable by an apparent molecular weight of about 17,000 on SDS-PAGE, an isoelectric point of pH 4.9 on LKB Ampholine PAG plate and a defined amino acid sequence.

BRIEF DESCRIPTION OF THE DRAWINGS

FIG. 5 shows the amino acid sequence of eight of the tryptic peptides illustrated in FIG. 4.

FIG. 6 illustrates three oligonucleotide probes derived from the sequence of tryptic peptides T18, T24, and T28 of bovine GMF. Beneath each amino acid is the corresponding nucleotide sequence derived from codon usage tables. This was used to generate an oligonucleotide probe which was then used to screen a human brain stem cDNA library for GMF clones.

FIG. 7 illustrates the cDNA sequence of human GMF. The GMF encoding open reading frame and flanking regions were sequenced by the chain termination method. The stop codon at the 3' end of the GMF encoding open reading frame is indicated by a dot. The single letter notation for amino acids is used: A, Ala; C, Cys; D, Asp; E, Glu; F, Phe; G, Gly; H, His; I, Ile; K, Lys; L, Leu; M, Met; N, Asn; P, Pro; Q, Gln, R, Arg; S, Ser; T, Thr; V, Val; W, Trp; Y, Tyr. Upper line, cDNA sequence; Lower line, deduced amino acid sequence. The amino acid composition of bovine GMF (R. Lim, unpublished), when compared to the deduced amino acid sequence, suggests that the amino terminus of GMF is near or at the methionine residue shown boxed.

DETAILED DESCRIPTION OF THE INVENTION

Previously described methods for the purification of GMF (Lim & Miller, *J. Cell. Physiol.*, 19: 255-259 (1984); Lim et al., *Biochemistry*, 24: 8070-8074 (1985)) consist of the following steps. Beef brains are homogenized and centrifuged to obtain the crude extract which is then fractionated with ammonium sulfate precipitation to obtain the proteins precipitated between 45% and 70% saturation. The material is further purified successively through DEAE SEPHACEL column and SEPHADEX G-75 column. It is then treated with a hydrosylapatite column employing a batchwise elution. Lastly, the sample is purified with C4 reverse-phase high performance liquid chromatography (HPLC) using a column which is 4.6 mm in diameter and 5 cm in length. Although the resulting product appeared to be homogeneous based on SDS polyacrylamide gel electrophoresis (PAGE), it was subsequently realized that the product was impure, containing several other proteins in addition to GMF. Because of the impurities, an amino acid sequence for the product was not obtainable.

Figure 1:
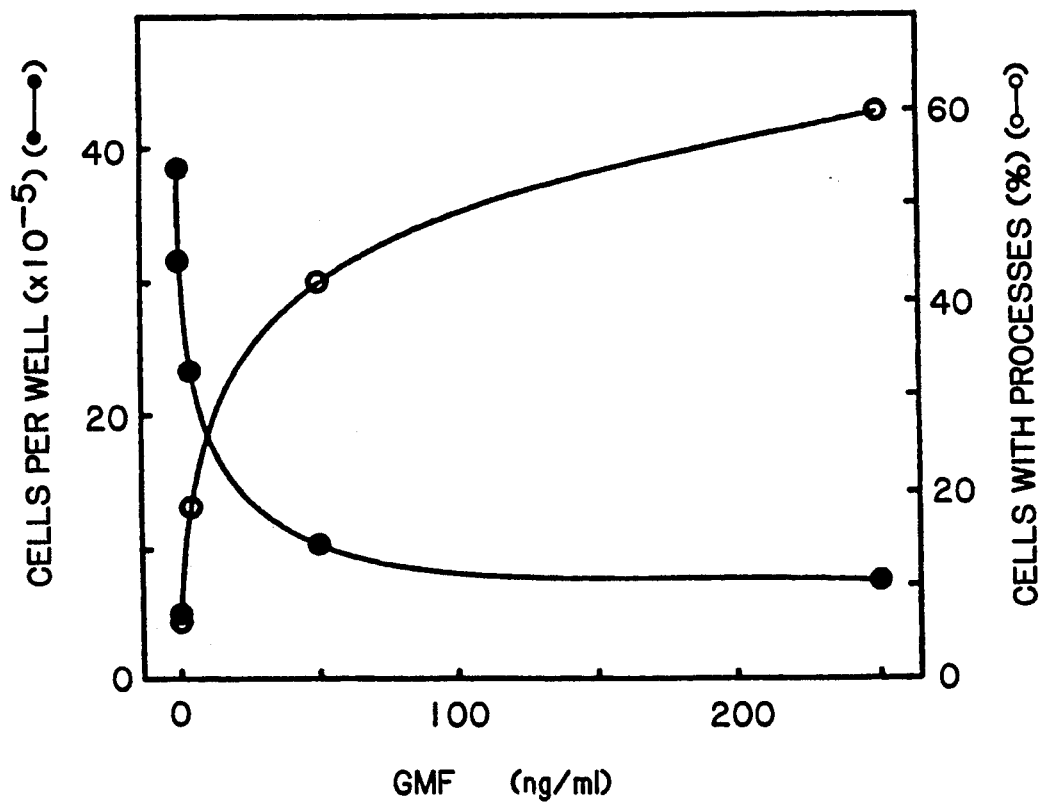
FIG. 1 shows the response of neuroblastoma (a neuronal tumor) cells in culture to GMF. As the dose of GMF increases, tumor cell proliferation (cells per well) decreases and cell differentiation (cells with processes) increases, indicating the ability of GMF to suppress tumor growth and to enhance neuronal differentiation.
Figure 2:
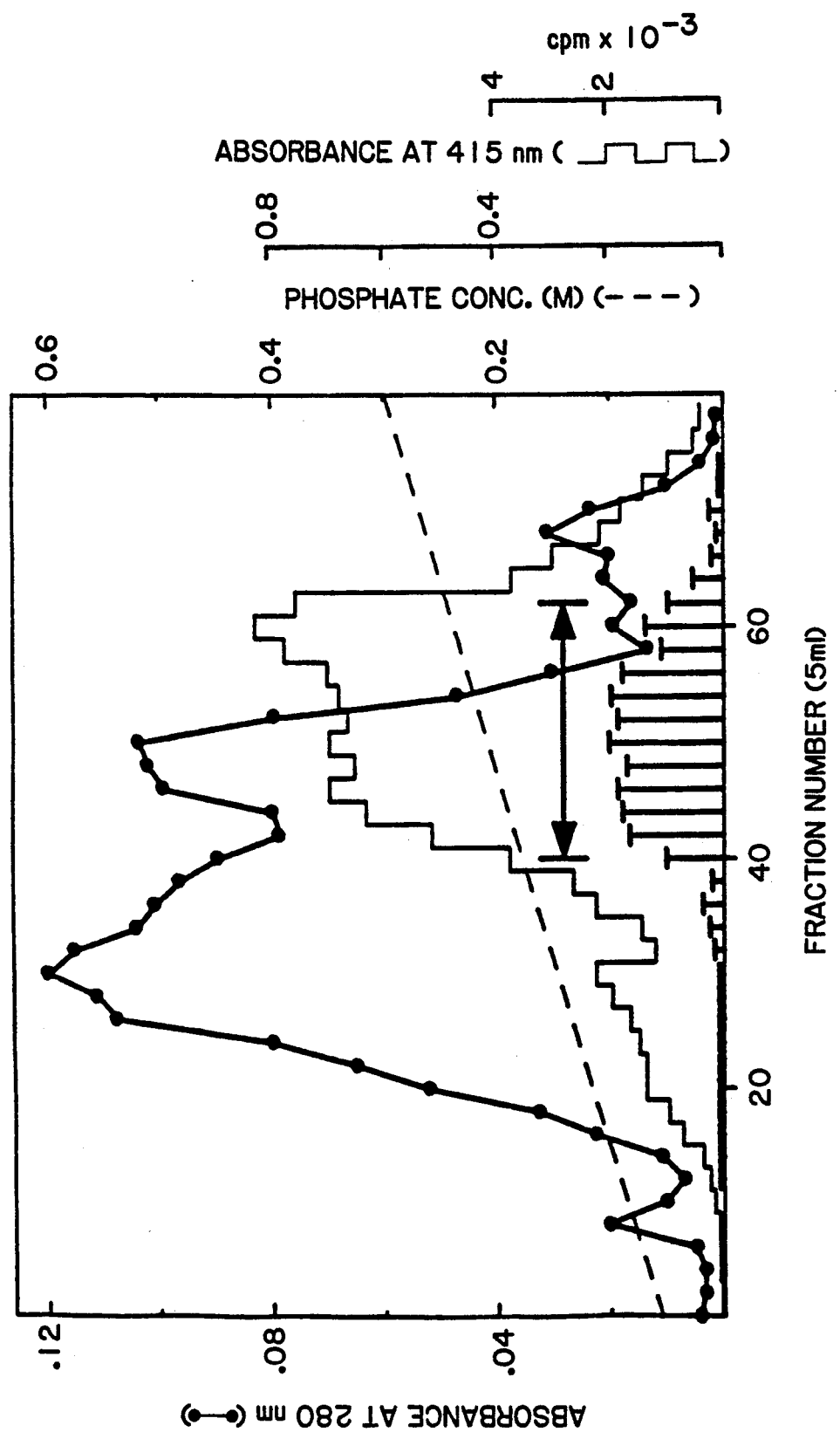
FIG. 2 is the elution profile of GMF sample treated by a gradient elution of hydroxylapatite column.
Figure 3:
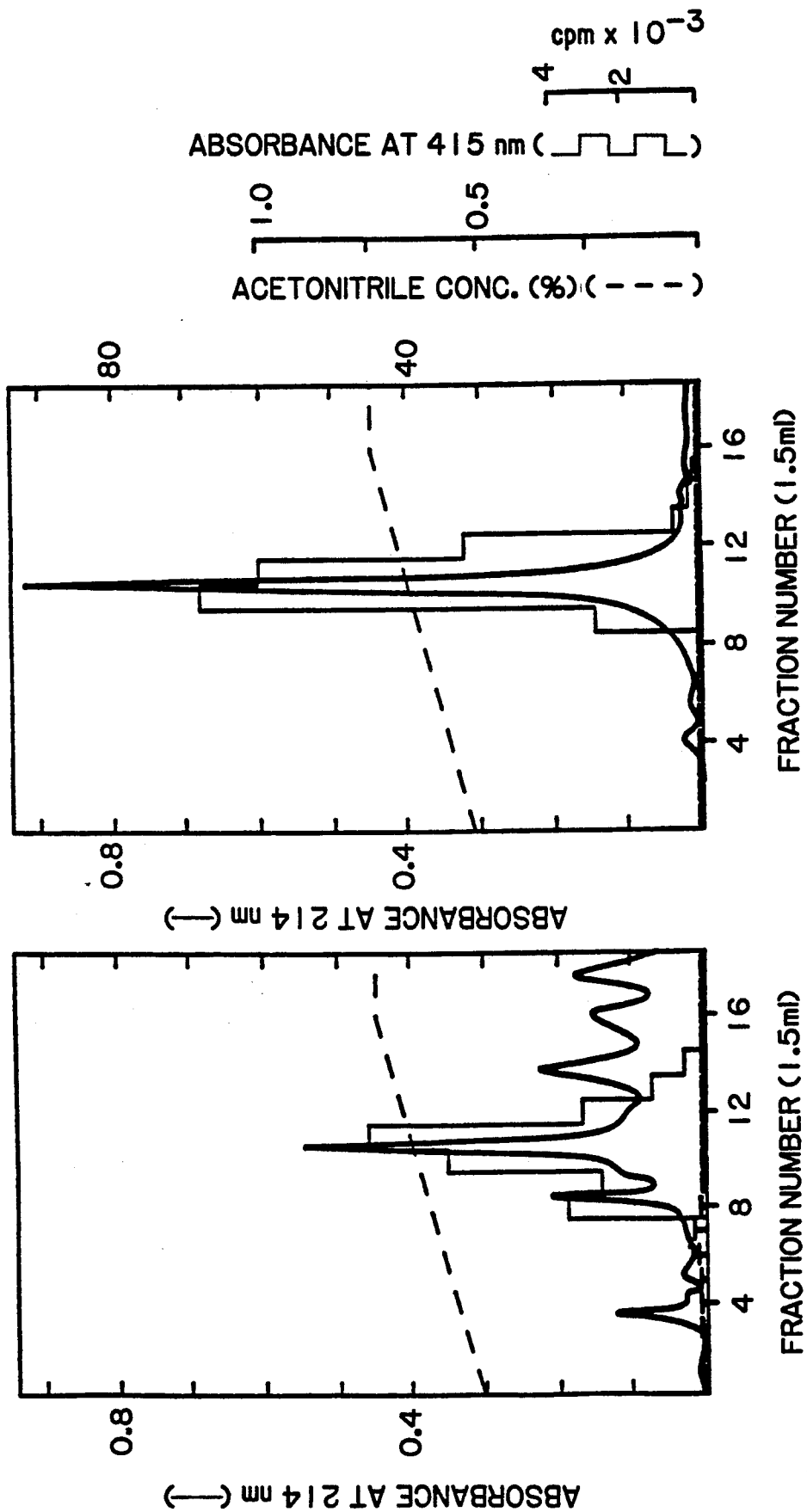
FIG. 3 is the elution profile of GMF sample in reverse-phase high performance liquid chromatography, showing that of initial chromatography (A) and of rechromatography (B). The latter step leads to the production of homogeneous natural GMF.
Figure 4:
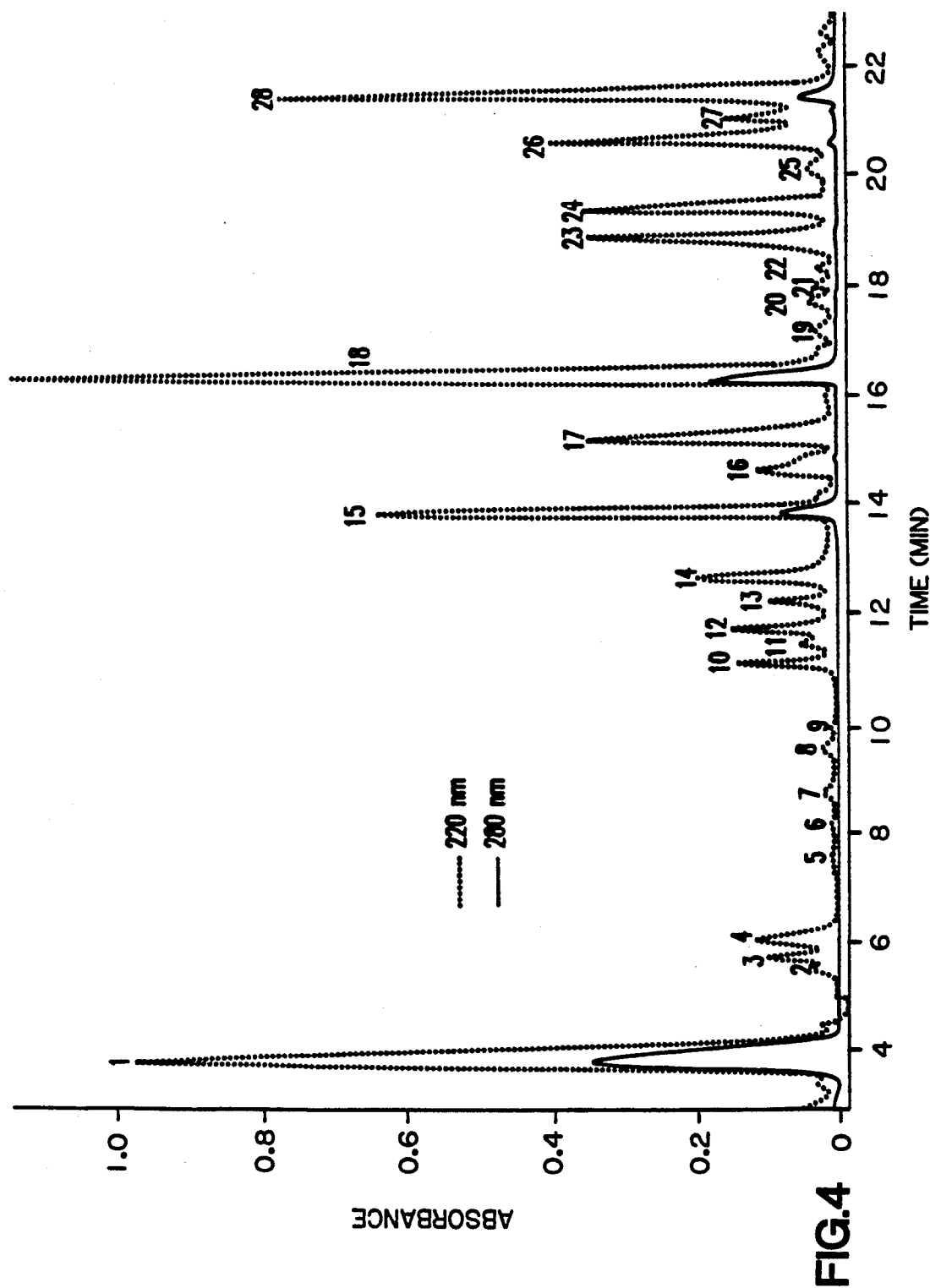
FIG. 4 illustrates the tryptic peptide map of GMF on HPLC, showing 28 peptide peaks.

The present invention incorporates several important changes to the above procedure. These are: (1) using a gradient elution (0.05M to 0.3M sodium potassium phosphate buffer at pH 7.45) instead of simple elution during the hydroxylapatite step in order to increase resolution (FIG. 2); (2) passing the post-hydroxylapatite sample through a heparin Sepharose column and collecting the protein fraction that does not bind to heparin, in order to eliminate all the heparin-binding proteins that contaminate the sample; (3) fractionating the post-heparin sample with C4 reverse-phase HPLC column, preferably 4.6 mm in diameter and 25 cm in length (instead of 5 cm in length), in order to increase resolution (FIG. 3). The combination of the above changes leads to the successful isolation of a homogeneous protein which is GMF. The pure GMF protein is biologically active and has an apparent molecular weight of about 17,000 when measured on SDS-PAGE. It has an isoelectric point of pH 4.9 on LKB Ampholine PAG plate. It reacts strongly with the monoclonal antibody G2-09. Rabbit polyclonal antibodies have also been produced against the pure GMF. Using either monoclonal or polyclonal antibodies, GMF shows practically no immunologic cross-reactivity with other proteins or growth factors, including the following: acidic and basic fibroblast growth factors, interleukin-I, tumor necrosis factor, nerve growth factor, insulin, insulin-like growth factor-II, epidermal growth factor and S-100 protein. The N-terminus is blocked. Digestion with trypsin releases 28 peptides (FIG. 4). Eight of these peptides have been sequenced and the results are shown in FIG. 5. A search through the Protein Identification Resource database revealed no identity or major homology with any of the known proteins, including other growth factors isolated from the brain.

Using the above-identified sequences of GMF typtic peptides, oligonucleotide probes (FIG. 6) were synthesized for the molecular cloning of GMF from a human brain stem cDNA library.

From the cDNA sequence the complete amino acid sequence of human GMF was deduced (FIG. 7). The deduced sequence contains all the partial sequences obtained from tryptic peptides of the natural bovine GMF. The deduced sequence of human GMF was checked through the Protein Identification Resource database, and, again, no major homology was found with any other known proteins. We, therefore, conclude that GMF is a unique protein, never identified before.

Assuming that translation of GMF mRNA is initiated at the methionine residue boxed in FIG. 7, the total amino acid residues deduced from the human cDNA adds up to 42, and the calculated molecular weight from this information is 16,716. This number is slightly smaller than the observed molecular weight of the natural GMF isolated from bovine brains. The slight discrepancy could be due to one or a combination of several possibilities: First, experimental error introduced during determination of molecular weight by SDS-PAGE. Second, bovine GMF may be a slightly longer polypeptide chain that the human counterpart. Third, natural GMF may contain non-amino acid moieties, such as carbohydrate. In any event, such minor variations do not interfere with the identity of the human GMF cDNA.

Recombinant GMF is produced by engineering a convenient restriction enzyme site adjacent or including the ATG translation initiation codon at the amino terminal methionine residue, followed by insertion of the modified GMF cDNA into an acceptable expression vector.

The biologically active GMF produced from natural sources or by the procaryotic or eucaryotic expression of cloned GMF genes can be used for the treatment of mammalian species by physicians and/or veterinarians. The preferred route of administration will depend on the condition being treated, and may include intraventricular administration for central nervous system (CNS) conditions, intravascular administration for peripheral conditions, and local application for both conditions. Considerations may be made to treat CNS conditions through vascular route provided that passage through the blood-brain barrier can be enhanced either by chemical modification of the GMF molecule, by pharmacological downgrading of the barrier, or by utilizing the pathological breakdown of the barrier resulting from the brain diseases to be treated. Chemical modification of the protein may enhance its half-life in the bloodstream or cerebrospinal fluid, thus increasing its therapeutic efficacy.

While GMF can be administered alone, it is preferable to present it as a pharmaceutical formulation, both for human and veterinary use. The formulation may comprise a pharmaceutically active amount of GMF protein with one or more of the pharmaceutically acceptable carriers and optionally other therapeutic ingredients. The carrier must be compatible with the other ingredients of the formulation and not deleterious to the recipient thereof. Suitable formulations may conveniently comprise sterile aqueous solutions of the active ingredient with solutions which are preferably isotonic with blood and cerebrospinal fluid of the recipient. Such formulations may be prepared by dissolving the solid ingredients in pyrogen-free water and rendering said solution sterile. The medicine may be presented in unit or multi-dose containers, such as sealed ampoules or vials.

The following examples are provided to aid in the understanding of the present invention. It is understood that modifications can be made in the procedures set forth, without departure from the invention.

EXAMPLE 1

Production of Pure Homogeneous GMF From Natural Source

The method incorporates the preliminary procedure previously described by Lim & Miller (*J. Cell. Physiol.*, 119: 255–259 (1984)), the disclosure of which is hereby incorporated by reference, and the final purification steps which constitute part of the current invention. The entire methods is as follows.

Beef brains are obtained from a slaughterhouse and stored frozen. Before use, the brains are partially thawed overnight in a cold room. All subsequent steps except HPLC are carried out at 4 degrees Celsius unless otherwise specified. After removing the meninges and surface blood vessels, the brains are cut into I-cm cubes and homogenized with a Waring blender in 0.02M Tris-HCl and 0.15M NaCl at pH 7.45 (Tris-buffered saline) at a ratio of 1 gram tissue/3 ml buffer, with setting at low speed for 30 seconds, then at high speed for another 30 seconds. The homogenate from 1 Kg beef brains is centrifuged for 1 hour at $20,000 \times g$ with a Beckman JA-10 rotor at 10,000 rpm or type 19 rotor at 15,000 rpm. The supernatant is cleared of debris by filtering through glass wool.

Ammonium sulfate is added to 45% saturation (25.8 g/100 ml). After stirring for 20 minutes, the precipitate is eliminated by centrifugation. An additional 15.6 g/100 ml of ammonium sulfate is added to bring the final saturation to 70%. After a second centrifugation, the pellet is dissolved in 100 ml Tris-buffered saline. The solution is dialyzed against 10 liters of water overnight, then against 10 liters of 0.02M Tris-HCl, pH 7.45, for at least 6 hours, using a Spectrapor-I membrane (molecular cutoff 6,000–8,000). The small amount of precipitate is removed by centrifugation.

The resulting supernatant, approximately 120 ml, is applied to a diethylaminoethyl (DEAE) SEPHACEL column, $2.5 \times 37$ cm. After washing with 4 column volumes of 0.02M Tris-HCl at pH 7.45, GMF activity is eluted with 1,300 ml of a linear gradient of 0–0.3M NaCl in 0.02M Tris-HCl, pH 7.45, at 40 ml/hour. At this point, the active fractions (440 ml) are pooled and concentrated to 50 ml by Amicon PM 10 membrane filtration. The concentrate is applied to a SEPHADEX G-75 column, $5 \times 100$ cm, and eluted with Tris-buffered saline at 40 ml/hour. The active fractions are pooled (500 ml).

The partially purified GMF sample (500 ml) from the SEPHADEX G-75 step is applied to a hydroxylapatite (Bio-Gel HT) column having a gel volume of 50 ml (5 cm diameter $\times 2.5$ cm height). After washing the charged column with 1 column volume of 0.15M NaCl in 0.02M Tris-HCl, pH 7.45, the bulk of the protein is eliminated with 150 ml of 0.05M potassium phosphate buffer at pH 7.45. This is followed by a gradient elution using 390 ml of potassium phosphate buffer (0.05M to 0.3M), pH 7.45, at a flow rate of 40 ml/hr (FIG. 2). The active fractions are pooled (120 ml).

The sample is divided into three portions. An aliquot of 40 ml is passed through a 5-ml heparin-SEPHAROSE column in order to eliminate contaminating proteins. Flow rate is set at 20 ml/hr. The heparin column is regenerated with 20 ml of 2M NaCl in 0.01M Tris-HCl, pH 7.0 and, before use, equilibrated with 20 ml of 0.1M potassium phosphate buffer at pH 7.45.

The heparin-treated sample (40 ml) is filtered through Millipore MILLEX GV (0.22 μm pore size) and adjusted to contain 0.1% trifluoroacetic acid (TFA). The sample is further divided into four portions. An aliquot of 10 ml is loaded on a Vydac $C_4$ reverse-phase HPLC column (4.6 mm×25 cm) (particle size 5 μm; pore size 300 Å) at a rate of 1.5 ml/min. The charged HPLC column is eluted at the same speed using the following program: 0% acetonitrile for 4 minutes, 0-30% acetonitrile gradient over 10 minutes, and finally 30-45% acetonitrile gradient over 15 minutes, all in the presence of 0.1% TFA. The major peak which emerges at 40 % acetonitrile and which reacts positively with the monoclonal antibody G2-09 is designated GMF (FIG. 3A).

The GMF peaks from four HPLC runs are pooled and purified once more through the same HPLC column. The pool is diluted 1:1 with water containing TFA to achieve a final concentration of 20% acetonitrile and 0.1% TFA. The sample is loaded on the column and eluted as before. The GMF peak obtained at this time, representing the yield form ⅓ of the starting material, is the final product (FIG. 3B).

EXAMPLE 2

Isolation of GMB cDNA Clones From a Human Brain Stem cDNA Library

A cDNA library constructed from the brainstem of a two-day old infant was previously described [DeFerra et al., Cell 43 721, (1985); Jaye et al., Science 233 541, (1986)]. To screen the library for recombinant phage containing GMF cDNA, $1 \times 10^6$ phage were plated on a lawn of E. coli Y1088 and incubated at 42 degrees Celsius for 5 hours. After the plates were refrigerated overnight, a nitrocellulose filter was overlaid on the plates. The position of the filter was marked with a needle. The filter was removed after one minute and left to dry at room temperature. From each plate, a duplicate filter was prepared exactly as described except that the filter was left in contact with the plate for five minutes. All filters were then prepared for hybridization as described in Maniatis et al., Cold Spring Harbor Laboratory, 1983. This involved DNA denaturation in 0.5M NaOH, 1.5M NaCl, neutralization in 0.75M Tris-HCl, pH 7.8, 1.5M NaCl, followed by 3× SSC (IX SSC is 0.15M NaCl, 20 mM sodium citrate, PH 7.0) and heating of the filters for 2 hours at 80 degrees Celsius in vacuo.

To screen the human brain stem cDNA library for clones containing GMF inserts, a specific oligonucleotide was designed. This oligonucleotide was based upon the amino acid sequence of tryptic peptide T28 (see FIGS. 5 and 6c) derived from bovine GMF. Two criteria were used in designing the GMF probe: 1) The dinucleotide CG was avoided. This strategy was based upon the observed underrepresentation of the CG dinucleotide in eukaryotic DNA [Josse et al., J. Biol. Chem. 236: 864-875 (1961)]; 2)( Preferred codon utilization data were used wherever possible. A comprehensive analysis of human codon utilization was found in Lathe, J. Mol. Biol. 183: 1-12 (1985). In addition, two other oligonucleotides, designed with the same strategy from other trypic peptides were contructed (see FIGS. 5 and 6a and 6b). The oligonucleotide based upon tryptic peptide T28 was chosen as probe for the initial library screen because it contained the fewest degenerate positions, on a percentage basis.

Approximately 100 pmoles of oligonucleotide T28 were radioactively labelled by incubation with $^{32}P$-gamma-ATP and T4 polynucleotide kinase, essentially as described by Maniatis et al., supra. Nitrocellulose filters prepared as described above were prehybridized at 40 degrees Celsius for several hours in 5X SSPE (IX SSPE is 0.18M NaCl, 0.01M $Na_2HPO_4$, pH 7.2, 0.001M EDTA), IX Blotto (Blotto is 0.25% nonfat dry milk), 0.2% sodium dodecyl sulfate (SDS). Approximately $1 \times 10^6$ cpm $^{32}P$-oligonucleotide per ml were added to fresh prehybridization solution and the filters were hybridized at 40 degrees Celsius overnight. Unhybridized probe was removed by sequential washing at 45 degrees Celsius with prewarmed 2X SSPE, 0.2% SDS and then with IX SSPE, 0.2% SDS.

From approximately one million plaques, 25 plaques gave positive autoradiographic signals after overnight exposure. The positive plaques were plugged and plated at low density (100~1 of a 10 4 dilution of each plug) using procedures described previously. The duplicate filters were cut into thirds and each third (in duplicate) was hybridized separately with oligonucleotides T18, T214 or T28. All hybridizations and washes were carried out as described previously.

Clones 7, 8, 10, 17A, 36, and 40 were chosen for further study, since each of these clones hybridized to two out of the three olignucleotides. None of the 25 clones tested hybridized unambiguously to all three oligonucleotides. The said aforementioned clones were plaque purified, the cDNA inserts removed by EcoRi digestion and then subcloned into the EcoRi site of M13mpl8. Upon sequencing by the chain termination method [Sanger et al. Proc. Natl. Acad. Sci. USA 74: 5463-5467 (1977)]. GMF clone 8 was found to contain the entire coding region as well as a portion of the 3' untranslated region. The nucleotide sequence of this clone and the amino acid sequence deduced form the nucleic acid sequence is shown in FIG. 7. The sequences of all of the sequenced tryptic peptides (FIG. 5) of bovine GMF are found in the deduced amino acid sequence of human &MF. The amino acid composition of bovine GMF shows 3 moles methionine per mole of GMF. This, together with the estimated molecular weight of bovine GMF (17,000) places the amino terminus of human GMF at or near the methionine residue shown boxed in FIG. 7 and predicts a molecular weight of approximately 16,716 for human GMF. Currently, it cannot be determined whether mature GMF derives from proteolytic processing of a larger polypeptide precursor at or near this methionine residue or from initiation of translation at this methionine residue. Further characterization of additional human GMF cDNA clones will reveal which mechanism is used. Thus, recombinant GMF can be produced by engineering a convenient restriction enzyme site adjacent to or including the ATG translation initiation codon at the amino terminal methionine residue, followed by insertion of the modified GMF cDNA into an acceptable expression vector.

Deposit of Strains Useful in Practicing the Invention

Biologically pure cultures of strains for practicing this invention are available at the offices of Rorer Biotechnology Inc.

Access to said cultures will be available during pendency of the patent application to one determined by the Commissioner to be entitled thereto under 37 C.F.R. Section 1.14 and 35 U.S.C. Section 122.

At a date prior to issuance a deposit of biologically pure cultures of the strains within the allowed claims will be made with the American Type Culture Collection, 12301 Parklawn Drive, Rockville, Md., the accession number indicated by amendment below, and the requisite fee will be paid.

All restrictions on availability of said culture to the public will be irrevocably removed upon the granting of a patent based upon the application, and said culture will remain permanently available for a term of at least five years after the most recent request for the furnishing of a sample and, in any case, for a period of at least 30 years after the date of the deposit. Should the culture become non-viable or be inadvertently destroyed, it will be replaced with a viable culture(s) of the same taxonomic description.

| Strain/Plasmid | ATCC No. | Deposit Date |
| --- | --- | --- |

What is claimed is:

1. A process for producing glia maturation factor comprising the amino acid sequence from 15 to 155 of FIG. 7 comprising, providing a replicable expression vector capable of expressing a DNA sequence encoding said glia maturation factor in a suitable host cell, transforming said host cell to obtain a recombinant host cell, and maintaining said recombinant host cell under conditions permitting expression of said GMF, and recovering said GMF.

2. The process according to claim 1 wherein said expression vector is a plasmid.

3. The process according to claim 2 wherein said plasmid is derived from pBR322.

4. The process according to claim 2 wherein a control function on said plasmid is provided by viral material.

5. The process according to claim 4 wherein said viral material is a member of the group consisting of bovine papilloma virus, Epstein Barr virus, adenovirus, Simian virus 40 and bacculovirus.

6. The process according to claim 1 wherein recovering said GMF comprises contacting the proteins expressed by the recombinant host cell with an antibody specific for GMF.

7. The process of claim 1 wherein said glia maturation factor is human glia maturation factor.

8. Glia maturation factor produced according to the process of claim 1.

9. A process for producing glia maturation factor comprising the amino acid sequence from 15 to 155 of FIG. 7, identifiable by an apparent molecular weight of about 17,000 on SDS-PAGE, an isoelectric point of about 4.9 on LKB Ampholine PAG plate and the defined amino acid sequence, comprising providing a replicable expression vector capable of expressing a DNA sequence encoding GMF in a suitable host cell, transforming said host cell to obtain a recombinant host cell, and maintaining said recombinant host cell under conditions permitting expression of said GMF. and recovering said GMF.

10. A replicable expression vector which comprises a DNA sequence encoding glia maturation factor (GMF), wherein said GMF comprises the amino acid sequence from 15 to 155 of FIG. 7.

11. A recombinant host cell transformed with the vector of claim 10.

12. The recombinant host cell according to claim 11 obtained by transforming a eukaryotic cell.

13. The recombinant host cell according to claim 11 obtained by transforming a member of the group consisting of *E. coli, B. subtilis,* insect cells, yeast, and vertebrate cells.

* * * * *

UNITED STATES PATENT AND TRADEMARK OFFICE
CERTIFICATE OF CORRECTION

PATENT NO.   :   5,270,452

DATED        :   December 14, 1993

INVENTOR(S)  :   Ramon Lim, Ruth Kaplan and Michael Jaye

It is certified that error appears in the above-identified patent and that said Letters Patent is hereby corrected as shown below:

TITLE PAGE:

In the Assignee [73] data, the following assignee was omitted:

University of Iowa Research Foundation, Iowa City, Iowa

Signed and Sealed this

Eighth Day of July, 1997

*Attest:*

BRUCE LEHMAN

*Attesting Officer*          Commissioner of Patents and Trademarks